United States Patent [19]

Pelan et al.

[11] 4,145,528

[45] Mar. 20, 1979

[54] PROCESS FOR PREPARING β-METHYLDIGOXIN

[75] Inventors: Borut Pelan; Marija Milohnoja; Magda Pezdirc, all of Ljubljana, Yugoslavia

[73] Assignee: LEK tovarna farmacevtskih in kemicnih izdelkov, n.sol.o., Ljubljana, Yugoslavia

[21] Appl. No.: 823,379

[22] Filed: Aug. 10, 1977

[30] Foreign Application Priority Data

Aug. 20, 1976 [YU] Yugoslavia .................. 2046/76

[51] Int. Cl.$^2$ .................................... C07J 17/00
[52] U.S. Cl. .................................... 536/7; 536/120; 536/5
[58] Field of Search .................. 536/5, 7, 120

[56] References Cited

U.S. PATENT DOCUMENTS

| | | | |
|---|---|---|---|
| 3,538,078 | 11/1970 | Kaiser et al. | 536/7 |
| 3,712,884 | 1/1973 | Voigtlander et al. | 536/7 |
| 3,753,974 | 8/1973 | Kaiser et al. | 536/7 |
| 3,753,975 | 8/1973 | Kaiser et al. | 536/7 |
| 3,816,403 | 6/1974 | Eberlein et al. | 536/5 |

*Primary Examiner*—Johnnie R. Brown
*Attorney, Agent, or Firm*—Pollock, Vande Sande & Priddy

[57] ABSTRACT

Preparation of β-methyldigoxin in the presence of dimethyl formamide, an inert solvent, methyl ester of a sulphuric acid, and strontium hydroxide.

7 Claims, No Drawings

PROCESS FOR PREPARING β-METHYLDIGOXIN

Methods for preparing digoxin monoalkylethers are known from patent literature. Dutch patent 68 13409 as well as German publication 1,961,043 and German publication of granted application 1,643,665 disclose the use of usual reagents, such as dialkyl sulphate and diazoalkane, for the partial monoalkylation of the hydroxy group in position 15 or 16 of the terminal digitoxose. By the application of dialkyl sulphate under the usual alkylation conditions as quoted in the Dutch patent, considerable quantities of undesirable polyethers are formed, which cannot be dealkylated and therefore cause a smaller yield of monoalkyletherification. On the other hand, the partial alkylation of digoxin with diazoalkanes, as exemplified in the same patent, is only practicable — because of the danger of explosion when using this reagent — on a laboratory scale.

The above-mentioned German patent literature which concerns the alkylation of digoxin includes some novelties which cause better yields and a greater selectivity of reactions if compared with the Dutch patent. This literature discloses that the success of the methylation of digoxin with dimethyl sulphate as methylating agent depends on the pH value of the reaction mixture, which can be adjusted by adding certain amounts of barium hydroxide. Of equal importance is the presence of aluminum isopropylate or aluminum oxide and of a neutral solvent, e.g. toluene. Said reagents stimulate the selectivity of the monomethylation reaction by directing the alkoxy group to the position 15 or 16 of the terminal digitoxose.

For the purification of crude β-methyldigoxin, which still contains some unreacted digoxin and minor impurities of α- and β-polymethyl digoxins, the above-mentioned German literature uses the method of multiple distribution between two solvent phases.

During our attempts of methylation of digoxin is dimethyl formamide solution, it was found that by using methylating agents, such as methyl ester of methane sulphonic acid (methyl mesylate) or methyl ester of p-toluene sulphonic acid (methyl tosylate), which are not mentioned by the above patent literature, and in the presence of strontium hydroxide, aluminum oxide and dioxane as reagents for regulating the pH value of the reaction mixture and for stimulating a selective course of digoxin methylation, there were achieved results — on condition that the process of the methyletherification is carried out in an inert atmosphere — which are of equal quality and in better yields, if compared with those disclosed by the German patent literature.

Further attempts of semisynthesis of β-methyldigoxin with dimethyl sulphate in the presence of aluminum oxide furnished evidence that the selective monomethylation of digoxin in position 16 of the terminal digitoxose in a dimethyl formamide solution, of compared with the data from German publication 1,961,034 and German publication of granted application 1,643,665, takes place with greater yields and in considerably shorter time, on the condition, however, that the reaction is carried out in an inert atmosphere and in the presence of strontium hydroxide and dioxane in amounts that are for about 50% smaller than those prescribed by the above-mentioned German literature for barium hydroxide and toluene, which are functionally analogous reagents. By the application of column chromatography on silica gel and the use of a mixture of a chlorinated hydrocarbon and alkanol as eluant, it is possible to isolate pure β-methyldigoxin form the reaction product which was previously partly purified in the usual way. The unreacted digoxin, which is recovered from the chromatographic purification, is remethylated.

Pure β-methyldigoxin as prepared according to the present process was identified by the TLC method, by determination of the melting point and by the IR spectra.

EXAMPLE 1

Digoxin (10 g.) is dissolved in a mixture of dimethyl formamide (80 ml.) and dioxane (80 ml.) and then strontium hydroxide (3.5 g.) and aluminum oxide (10 g., activity 1-2 according to Brockmann) are added. To this suspension methyl mesylate (9.3 g.), dissolved in dioxane (80 ml.) is added dropwise within one hour in the presence of an inert gas and under stirring. After the addition of the methylating agent is completed, the reaction mixture is stirred for further 5 hours, then chloroform (160 ml.) is added, the precipitate is filtered off, washed with chloroform (100 ml.), pyridine (40 ml.) is added to the filtrate, which is then concentrated in vacuo to an oily residue. The latter is diluted with chloroform (300 ml.) and extracted four times with distilled water (40 ml. portions). The combined chloroform extracts are dried with anhydrous sodium sulphate and then concentrated in vacuo to a dry residue. Thereform β-methyldigoxin is eluted on a $SiO_2$ column with a chloroform/ethanol mixture (93:7). After recrystallization from ethyl acetate, saturated with water, the yield of β-methyldigoxin is 6.7 g.; m.p. 225°-229° C. IR spectrum is identical with the spectrum of standard methyldigoxin.

EXAMPLE 2

Digoxin (10 g.) is dissolved in dimethyl formamide (80 ml.), then dioxane (40 ml.), strontium hydroxide (3.5 g.) and aluminum oxide (10 g., activity 1-2 according to Brockmann) are added. Methyl tosylate (12 g.), dissolved in dioxane (40 ml.) is added dropwise to this suspension within 60 minutes in the presence of an inert gas and under stirring at room temperature. After stirring for further 12 hours, the same procedure as described in Example 1 is applied. The crude product of monomethylation is purified by column chromatography. Adsorbent $SiO_2$, eluant: methylene chloride/methanol (95:5). The combined β-methyldigoxin fractions are dried in vacuo and recrystallized from a mixture of methylene chloride/carbon tetrachloride (1:8). The yield of β-methyldigoxin 6.6 g., m.p. 225°-229° C. IR spectrum is identical with the spectrum of standard methyldigoxin.

EXAMPLE 3

Digoxin (60 g.) is dissolved in a mixture of dry dimethyl formamide (480 ml.) and dioxane (240 ml.) and then strontium hydroxide (19.8 g.) and aluminum oxide (36 g., activity 1-2 according to Brockmann) are added. In the presence of an inert gas and under stirring at room temperature, freshly distilled dimethyl sulphate (45 ml.), dissolved in dioxane (240 ml.) is added dropwise within 2 hours. After the addition of the methylating agent is completed, the reaction mixture is stirred in an inert atmosphere for further 2 hours, then chloroform (1200 ml.) is added, the precipitate is sucked off and washed with chloroform (600 ml.). Pyridine (270 ml.) is added to the filtrate, the filtrate is evaporated in vacuo to a thick oily residue, which is dissolved in chlorofrm (1.8 l.) and extracted four times with water (240 ml. portions). The combined and dried chloroform extracts are evaporated in vacuo to a dry residue, from which on a SiO$_2$ column β-methyldigoxin fractions are extracted with a mixture of methylene chloride/methanol (95:5). These fractions are evaporated in vacuo to a dry residue, which is recrystallized from a mixture of acetone/petroleum ether (97:3). The yield of β-methyldigoxin is 40 g., m.p. 225°–229° C. IR spectrum is identical with the spectrum of standard methyldigoxin.

What is claimed is:

1. In a process for preparing β-methyldigoxin by selective monomethyletherification of digoxin in a dimethyl formamide solution wherein the improvement comprises carrying out the reaction in an inert atmosphere using methyl esters of organic or inorganic sulphuric acids as methylating agents in the presence of strontium hydroxide and in addition to said dimethyl formamide in the presence of an inert solvent at ambient temperature, and isolating said β-methyldigoxin from the purified crude methylation product by column chromatography on SiO$_2$ with a mixture of a chlorinated hydrocarbon and a lower alkanol.

2. The process of claim 1 wherein said methylating agent includes a methyl ester of an organic sulphuric acid.

3. The process of claim 1 wherein said methylating agent includes methyl ester of p-toluene sulphuric acid (methyl tosylate).

4. The process of claim 1 wherein said methylating agent includes methyl ester of methane sulphuric acid (methyl mesylate).

5. The process of claim 1 wherein said inert solvent is dioxane.

6. The process of claim 1 wherein aluminum oxide is employed.

7. The process of claim 1 wherein a mixture of chloroform/ethanol or a mixture of methylene chloride/methanol is used as eluant in the column chromotography of crude β-methyldigoxin.

* * * * *